United States Patent [19]

Harada

[11] 4,001,225
[45] Jan. 4, 1977

[54] PYRIDYL SUBSTITUTED 7-αESTERS OF 3 HETEROTHIO 7-ACETAMIDO CEPHALOSPORANIC ACIDS
[75] Inventor: Hirokichi Harada, Nishinomiya, Japan
[73] Assignee: Fujisawa Pharmaceutical Co., Ltd., Osaka, Japan
[22] Filed: Jan. 30, 1975
[21] Appl. No.: 545,342

Related U.S. Application Data
[63] Continuation-in-part of Ser. No. 476,037, June 3, 1974.
[52] U.S. Cl. .............................. 260/243 C; 424/246
[51] Int. Cl.² ...................................... C07D 501/36
[58] Field of Search ................................ 260/243 C

[56] References Cited
UNITED STATES PATENTS
3,812,116    5/1974    Takano et al. ................. 260/243 C Primary Examiner—Nicholas S. Rizzo
Assistant Examiner—David E. Wheeler
Attorney, Agent, or Firm—Dayton R. Stemple, Jr.

[57] ABSTRACT

This invention relates to new cephalosporanic acid derivatives and pharmaceutically acceptable salts thereof which possess antibacterial activity, pharmaceutical composition of the same and processes for the preparation thereof.

8 Claims, No Drawings

PYRIDYL SUBSTITUTED 7-αESTERS OF 3 HETEROTHIO 7-ACETAMIDO CEPHALOSPORANIC ACIDS

This application is a continuation-in-part of Ser. No. 476,037, filed June 3, 1974.

The cephalosporanic acid derivatives of this invention can be represented by the following general formula:

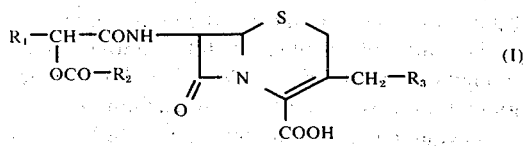

wherein $R_1$ is hydrogen, aryl or a heterocyclic group, $R_2$ is pyridyl or styryl and $R_3$ is hydrogen, alkylthio or a heterocyclic-thio group, in which the heterocyclic-thio group may be substituted with alkyl.

The term "aryl" represented by $R_1$ includes phenyl, naphthyl, tolyl, xylyl, mesityl, cumenyl, and the like.

The term "a heterocyclic group" represented by $R_1$ includes a residue of furan, thiophene, pyrrole, pyrazole, imidazole, triazole, thiazole, isothiazole, oxazole, isoxazole, thiadiazole, oxadiazole, thiatriazole, oxatriazole, pyridine, pyrazine, pyrimidine, pyridazine, benzothiophene, benzofuran, indole, indazole, benzimidazole, benzothiazole, benzothiadiazole, benzoxazole, purine, quinoline, isoquinoline, phthalazine, naphthyridine, quinoxaline, quinazoline, pyrrolidine, imidazolidine, piperidine, piperazine, and the like.

The term "alkylthio" represented by $R_3$ includes methylthio, ethylthio, propylthio, isopropylthio, butylthio, isobutylthio, tertbutylthio, pentylthio, hexylthio and the like.

The term "a heterocyclic-thio group" represented by $R_3$ includes a residue of a thiol compound having a heterocyclic group, in which the heterocyclic group means a residue of furan, thiophene, pyrrole, pyrazole, imidazole, triazole, thiazole, isothiazole, oxazole, isoxazole, thiadiazole, oxadiazole, thiatriazole, oxatriazole, tetrazole, pyridine, pyrazine, pyrimidine, pyridazine, benzothiophene, benzofuran, indole, indazole, benzimidazole, benzothiazole, benzothiadiazole, benzoxazole, purine, quinoline, isoquinoline, pthalazine, naphthyridine, quinoxaline, quinazoline, pyrrolidine, imidazolidine, piperidine, piperazine, and the like. The heterocyclic moiety of the heterocyclic-thio group may be substituted with one or more alkyl groups, such as methyl, ethyl, propyl, isopropyl, butyl, isobutyl, tert-butyl, pentyl, hexyl, and the like.

The term "pharmaceutically acceptable salt" of the compounds (I) includes a metal (e.g. sodium, potassium, magnesium, etc.) salt, an organic amine (e.g., methylamine, diethylamine, trimethylamine, triethylamine, aniline, pyridine, picaline, N,N'-dibenzylethylenediamine, etc.) salt and the like.

The objective cephalosporanic acid derivatives (I) may be prepared by reacting 7-amino-3-substituted-3-cephem-4-carboxylic acids of the general formula:

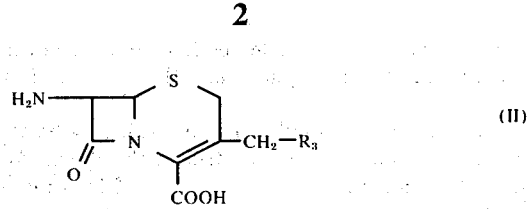

wherein $R_3$ is as defined above, or their derivatives at the amino group and/or the carboxy group, or salts thereof, with carboxylic acids of the general formula:

wherein $R_1$ and $R_2$ are as defined above, their reactive derivatives at the carboxy group, or salts thereof.

The derivative at the amino group of the compound (II) may be a reaction product of the compound (II) and a silyl compound such as bis[(lower)alkylsilyl]acetamide (e.g., bis(trimethylsilyl)acetamide, etc.) or the like.

The derivative at the carboxy group of the compound (II) may be an ester such as alkyl ester (e.g. methyl ester, ethyl ester, propyl ester, butyl ester, pentyl ester and the like), trimethylsilyl ester, 2-mesylethyl ester, 2-iodoethyl ester, 2,2,2-trichloroethyl ester, benzyl ester, 4-methoxybenzyl ester, 4-nitrobenzyl ester, phenacyl ester, phenethyl ester, trityl ester, diphenylmethyl ester, bis(methoxyphenyl)methyl ester, 3,4-dimethoxybenzyl ester, (1-cyclopropyl)ethyl ester, ethynyl ester, 4-hydroxy3,5-di-tert-butylbenzyl ester, etc.; an activated amide; an acid anhydride; an acid halide, or the like.

The salt of the compound (II) may be a metal (e.g., sodium, potassium, magnesium, calcium, etc.) salt, an organic amine (e.g., methylamine, diethylamine, trimethylamine, triethylamine, aniline, pyridine, picoline, N,N'-dibenzylethylenediamine, etc.) salt, an inorganic acid salt (e.g., hydrochloride, sulfate, etc.), an organic acid salt (e.g., acetate, maleate, tartrate, benzenesulfonate, toluenesulfonate, etc.) or the like.

The reactive derivative at the carboxy group of the carboxylic acids (III) may be an acid halide, an acid anhydride, an activated amide, an activated ester, or the like. The suitable examples may be an acid chloride, an acid azide; a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid) or aromatic carboxylic acid (e.g., benzoic acid), or a symmetrical acid anhydride; an acid amide with imidazole, 4-substituted imidazole, dimethylpyrazole, triazole or tetrazole; or an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide or N-hydroxyphthalimide), or the like. The suitable derivative can be optionally selected from them according to the kind of the carboxylic acids (III) to be used practically.

The reaction is usually carried out in a solvent such as acetone, dioxane, acetonitrile, chloroform, methylene chloride, ethylene chloride, tetrahydrofuran, ethyl acetate, dimethylformamide, pyridine or any other organic solvent inert to the reaction. Among these solvents, hydrophilic solvents may be used in a mixture with water.

When the carboxylic acids (III) are used in a form of the free acid or salt in this reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intramolecular salt, (chloromethylene)dimethylammonium chloride, and the like. The salt of the carboxylic acids (III) may be an alkali metal salt, an alkaline earth metal salt, an ammonium salt, a salt with an organic base such as trimethylamine, dicyclohexylamine or the like.

Also, when the carboxylic acids (III) in free form are employed, the reaction may be preferably carried out in the presence of a base such as alkali metal bicarbonate, trialkylamine, N,N-dialkylbenzylamine, pyridine, and the like. When the base of the condensing agent is in liquid, it can be used also as a solvent. The reaction temperature is not restrictive, and the reaction is usually carried out under cooling or at room temperature.

The derivatives at the amino group and the carboxy group in the compounds (II) may be converted to their free form in the course of the reaction of the compounds (II) and the carboxylic acids (III), and this conversion is also included in the scope of the present invention as a variation of the processes. And, some derivatives at the carboxy group of the compounds (II) remaining without being subjected to such conversion result in the derivatives at the carboxy group of the object compounds (I) according to the reaction, which can be converted to the free carboxylic acid of the object compounds (I) according to conventional methods.

Some of the object compounds (I) may be also prepared by reacting 7-substituted-3-alkanoyloxymethyl-3-cephem-4-carboxylic acids of the general formula:

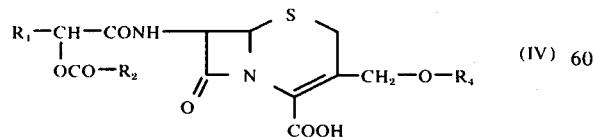

(IV)

wherein
$R_1$ and $R_2$ are as defined above and
$R_4$ is alkanoyl, or its their derivatives at the carboxyl group, or salts thereof, with thiol compounds of the general formula:

$$R_3' - H \qquad (V)$$

wherein $R_3'$ is alkylthio or a heterocyclic-thio group, in which the heterocyclic-thio group may be substituted with alkyl, or their alkali metal salts.

The term "alkanoyl" represented by $R_4$ in the formula (IV) includes formyl, acetyl, propionyl, butyryl and the like.

The derivatives at the carboxy group can be referred to the above description for the compounds (II).

The salts of 7-substituted-3-alkanoyloxymethyl-3-cephem-4-carboxylic acids (IV) may be a metal (e.g., sodium, potassium, magnesium, calcium, etc.) salt, an organic amine (e.g., methylamine, diethylamine, trimethylamine, triethylamine, aniline, pyridine, picoline, N,N'-dibenzylethylenediamine, etc.) salt or the like.

The term "alkylthio" and "a heterocyclic-thio group" in the formula (V) can be referred to the descriptions given above to these terms for $R_3$.

The alkali metal salt of the thiol compounds (V) may be a sodium salt, a potassium salt, or the like.

The reaction of the 7-substituted-3-alkanoyloxymethyl-3-cephem-4-carboxylic acids (IV) or, their derivatives at the carboxy group, or salts thereof, with the thiol compounds (V) or the alkali metal salts thereof may be carried out in a solvent such as water, acetone, chloroform, nitrobenzene, dimethylformamide, methanol, ethanol, dimethylsulfoxide, or any other organic solvents inert to the reaction, preferably in a strongly polar solvent. Among the solvents, hydrophilic solvents may be used in a mixture with water. The reaction is preferably carried out in around neutral medium. When the compound (IV) or the thiol compound (V) is used in a free form, the reaction is preferably conducted in the presence of a base such as alkali metal hydroxide, alkali metal carbonate, alkali metal bicarbonate, trialkylaine, and the like. The reaction temperature is not restrictive, and the reaction is usually carried out at room temperature or under warming. The reaction product can be isolated from the reaction mixture by conventional methods.

The derivatives at the carboxy group in the formula (IV) are converted to their free form in the course of the reaction, and this conversion is also included in the scope of the present invention as a variation of the processes. And, some derivatives at the carboxy group of the compounds (IV) remaining without being subjected to such conversion result in the derivatives at the carboxy group of the object compounds (I) according to the reaction, which can be converted to the free carboxylic acid of the object compounds (I) according to conventional methods.

All the reactants to be employed in the various processes of the present invention may be commercially available or be prepared by conventional methods well known to the art or by a variety of analogous methods applicable to production of such reactants. Reference may be had to the preparation of the starting compounds (III) mentioned below.

Some of the starting compounds (III) can be produced, for example, by reacting the compound of the formula:

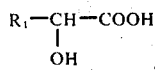

wherein $R_1$ is as defined above, with the compound of the formula:

$$R_2 - COOH \qquad (IV)$$

wherein $R_2$ is as defined above, or its reactive derivative.

The reactive derivative of the compound (IV) may be same as the reactive derivative at the carboxy group of the carboxylic acids (III).

THE PREPARATION OF THE STARTING COMPOUNDS i. To a solution of D,L-2-(2-thienyl)glycolic acid (3.2 g.) in pyridine (20ml.) was added cinnamoyl chloride (3.6 g.) and then the mixture was stirred at room temperature for 4 hours. The resultant solution was concentrated under reduced pressure. The residue was added with water (30ml.), adjusted to pH 8.0 with a sodium bicarbonate aqueous solution and then was washed with ether (200ml.) three times. The aqueous solution was adjusted to pH 1.0 with 10% hydrochloric acid, and then extracted with ether (30ml.) three times. The extract was dried over sodium sulfate and concentrated under reduced pressure. The residue was crystalized with ether and filtered to give white crystals (4.2 g.) of D,L-2-cinnamoyloxy-2-(2-thienyl)acetic acid.

IR: $\nu^{nujol}(cm^{-1})$ : 1150, 1625, 1640, 1680, 1720, 1730 ii. To a solution of D-2-phenylglycolic acid (18.4 g.) in pyridine (80ml.) was added a solution of cinnamoyl-chloride (20.1 g.) in methylene chloride with stirring at 0° to 5° C and stirred at the same temperature for 30 minutes, at room temperature for 1 hour and then at 60° C for 2 hours. After filtration of the resultant mixture, the filtrate was concentrated under reduced pressure. The residue was added with water (40ml.), adjusted to pH 2.0 with concentrated hydrochloric acid and then extracted with ether. The extract was washed with 5% hydrochloric acid and a saturated aqueous solution of sodium chloride in turn and then dried. The solvent was distilled off under reduced pressure from the extract to give reddish oil (39.5 g.) of D-2-cinnamoyloxy-2-phenylacetic acid.

iii. To a solution of glycolic acid (15.2 g.) in pyridine (100ml.) was added cinnamoyl chloride (33.4 g.) with stirring under cooling. The reaction mixture was stirred at room temperature for 5 hours and concentrated under reduced pressure at 50° to 60° C. The residue was adjusted to pH 1 with concentrated hydrocloric acid and extracted with ether. The extract was washed with water and a sodium chloride aqueous solution, in turn and concentrated under reduced pressure to give colorless crystals (45 g.). These crystals were dissolved in a sodium bicarbonate aqueous solution and adjusted to pH 3 to 3.5 with aqueous hydrochloric acid and extracted with ether. The extract was treated with a conventional manner to give crude product (16.5 g.). The product was recrystallized from benzene to give a product of 2-cinnamoyloxyacetic acid (10.4 g.), m.p. 116° to 121° C.

iv. To a solution of 2-(2-thienylglycolic acid (5.0 g.) in dry dioxane (50ml.) was added isonicotinic acid anhydride (7.2 g.) and the resultant mixture was stirred at 80° C for 8 hours. The reaction mixture was filtered and the filtrate was concentrated under reduced pressure. The residue was dissolved in acetone and the solution was filtered to remove insoluble substances. To the filtrate was added 28% hydrochloric acid in ethanol (3.0ml.), and the solution was concentrated under reduced pressure. The residue was washed with ether three times. Addition of acetone thereto and trituration gave powder (2.8 g.) of hydrochloric acid salt of 2-isonicotinoyloxy-2-(2-thienyl)acetic acid, m.p. 145° C (dec.).

v. To a solution of 2-(2-thienyl)glycolic acid (10.5 g.) in dry dioxane (100ml.) was added nicotinic acid anhydride (15.3 g.) and the mixture was stirred at 80° C for 10 hours. After filtration of the resultant mixture, the filtrate was concentrated under reduced pressure. The residue was dissolved in acetone and insoluble substances were removed by filtration. To the mother liquid was added 28% hydrochloric acid in ethanol (6ml.) and the solution was concentrated. The residue was added with acetone, pulverized and then filtered to give powder. The powder was suspended in acetone and filtered to give hydrochlorid acid salt (8.0 g.) of 2-nicotinoyloxy-2-(2-thienyl)acetic acid, m.p. 150° C (dec.).

In accordance with the present invention, a precipitate which forms during the reaction is separated from the reaction mixture by methods commonly used for this purpose, and the resulting reaction product may be subjected to routinely used purification procedures, for instance, to recrystallization from an appropriate solvent or a mixture of such solvents.

The compounds of the present invention may be converted by conventional methods into their pharmaceutically acceptable, substantially non-toxic salts.

The compounds of the present invention exhibit high antibacterial activity and inhibit the growth of a number of microorganisms including Gram-positive and Gram-negative bacteria. For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral or parenteral administration. The pharmaceutical preparations may be in solid form such as capsules, tablets, or dragees, or in liquid form such as solutions, suspensions, or emulsions. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 100 mg., 250 mg., and 500 mg. of the compounds according to the present invention has proved to be effective in treating diseases caused by bacterial infection. In general amounts between 10 mg. and about 1000 mg. or even more may be administered.

The following examples are given for the purpose of illustrating the present invention:

EXAMPLE 1

A mixture of dimethylformamide (0.88 g) and thionyl chloride (2 ml.) was stirred at 40° C. for 30 minutes and then the excess of thionyl chloride was distilled off under reduced pressure. Addition of dried ether and methylene chloride to the residue and evaporation thereof were repeated to give white crystals. The crystals were suspended in methylene chloride (20 ml.), and to the suspension was added hydrochloric acid salt of DL-2-phenyl-2-picolinoyloxy-acetic acid (2.93 g.) at room temperature and the mixture was stirred for 2.5 hours.

On the other hand, 7-amino-3-methyl-3-cephem-4-carboxylic acid (2.14 g.) was suspended in methylene chloride (10 ml.) and to the suspension was added a solution (18.6 ml.) of N-trimethylsilylacetamide in methylene chloride (1 mole/372 ml.). To the solution was added the solution obtained above all at once with stirring vigorously under ice-cooling and then the mixture was stirred at room temperature for 2 hours. The solvent was distilled off from the reaction mixture under reduced pressure and then to the residue was added ice-water. The precipitating crystals were collected by filtration, washed with water and then dissolved in an adequate amount of an aqueous sodium bicarbonate. The solution was treated with activated charcoal powder and then filtered. The filtrate was adjusted to pH 3.5 with diluted hydrochloric acid and the precipitate was collected by filtration, washed with water and dried to give 7-(DL-2-phenyl-picolinoyloxyacetamide)-3-methyl-3-cephem-4-carboxylic acid (3.7 g.), m.p. 134° to 145° C (dec.).

U.V.: $\lambda_{max}^{phosphate\ buffer\ (pH\ 6.4)}$ 265 m$\mu$, E=272

EXAMPLE 2

A mixture of dimethylformamide (0.88 g.) and thionyl chloride (2.0 ml.) was heated for 30 minutes at 50° C, and then the excess of thionyl chloride was distilled off under reduced pressure. Ether was added to the residue and the mixture was allowed to stand for a while and then the solvent was distilled off, which were repeated three times. Thus obtained residue was suspended in methylene chloride (30 ml.), and to the suspension was added hydrochloric acid salt of D-2-phenyl-2-nicotinoyloxyacetic acid (2.4 g.) under ice-cooling, and then the mixture was stirred for 3 hours at room temperaure.

On the other hand, to methylene chloride (30 ml.) were added 7-amino-3-methyl-3-cephem-4-carboxylic acid (2.14 g.) and a solution of N-trimethylsilylacetamide in methylene chloride (1 mole/372 ml.) (13 ml.), and then the mixture was stirred for 4 hours at room temperature. To the solution was added the solution obtained above all at once under ice-water cooling, and then the mixture was stirred for 3.25 hours at the same temperature. The reaction mixture was allowed to stand for overnight in a freezer and then concentrated. To the residue were added ice-water and ethyl acetate in turn, and then insoluble material was collected by filtration and washed with ethyl acetate to give 7-(D-2-phenyl-2-nicotinoyloxyacetamido)-3-methyl-3-cephem-4-carboxylic acid (2.5g.), m.p. 200° to 201° (dec.).

EXAMPLE 3

A mixture of dimethylformamide (0.42 g.) and thionyl chloride (2.5 ml.) was heated for 30 minutes at 50° C, and the excess of thionyl chloride was distilled off under reduced pressure. Ether was added to the residue, and the mixture was allowed to stand for a while and then the solvent was distilled off, which were repeated twice. And then the similar operations were repeated twice by using methylene chloride instead of ether. Thus obtained white residue was suspended in methylene chloride (20 ml.), and to the suspension was added hydrochloric acid salt of D-2-phenyl-2-isonicotinoyloxyacetic acid (1.7 g.) under ice-cooling, and then the mixture was stirred for 2.5 hours at room temperature.

On the other hand, to methylene chloride (15 ml.) were added 7-amino-3-methyl-3-cephem-4-carboxylic acid (1.1 g.) and a solution of N-trimethylsilyacetamide (6.5 ml.) in methylene chloride (1 mole/372 ml.), and the mixture was stirred for 4 hours at room temperature. To the solution was added the solution obtained above all at once under ice-cooling, and then the mixture was stirred for 1.5 hours at the same temperature. The reaction mixture was concentrated. To the residue was added ice-water followed by operations of scrubbing the wall of a vessel and decantation which were repeated several times. Thus obtained powder was collected by filtration, washed with water and dried to give 7-(D-phenyl-2-isonicotinoyloxyacetamido)-3-methyl-3-cephem-4-carboxylic acid (1.4 g.), m.p. 140° to 150° C (dec.).

EXAMPLE 4

A mixture of dimethylformamide (0.9 g.) and thionyl chloride (1.4 g.) was stirred for 30 minutes at 50° C, and then the excess of thionyl chloride was distilled off under reduced pressure. Ether was added to the residue, and the mixture was allowed to stand for a while and then the solvent was distilled off, which were repeated twice. And then the similar operations were repeated three times by using methylene chloride instead of ether. Thus obtained white powder was suspended in methylene chloride (40 ml.), and to the suspension was added hydrochloride acid salt of DL-2-(2-thienyl)-2-isonicotinoyloxyacetic acid (3.0 g.) under ice-cooling, and then the mixture was stirred for 2 hours at room temperature.

On the other hand, to methylene chloride (30 ml.) were added 7-amino-3-methyl-3-cephem-4-carboxylic acid (2.14 g.) and a solution (16 ml.) of N-trimethysilylacetamide in methylene chloride (1 mole/372 ml.), and the mixture was stirred for 4 hours at room temperature. To the solution was added the solution obtained above all at once under ice-cooling, and the reaction mixture was stirred for 3 hours at the same temperature. The reacting mixture was concentrated and to the residue was added water. The powder precipitated by scrubbing the wall of a vessel was collected by filtration, washed with water and dried to give 7-{DL-2-(2-thienyl)-2-isonicotinoyloxyacetamido}-3-methyl-3-cephem-4-carboxylic acid (3.7 g.), m.p. 160° C (dec.).

EXAMPLE 5

A mixture of dimethylformamide (0.7 g.) and thionyl chloride (1.24 g.) was stirred for 30 minutes at 50° C, and then the excess of thionyl chloride was distilled off under reduced pressure. Ether was added to the residue, and the mixture was allowed to stand for a while and then the solvent was distilled off, which were repeated twice. And then the similar operations were repeated twice by using methylene chloride instead of ether. Thus, obtained white substance was suspended in methylene chloride (30 ml.), and to the suspension was added hydrochloric acid salt of DL-2-(2-thienyl)-2-nicotinoyloxyacetic acid (2.4 g.) under ice-cooling, and then the mixture was stirred for 2.5 hours at room temperature.

On the other hand, to methylene chloride (24 ml.) were added 7-amino-3-methyl-3-cephem-4-carboxylic acid (1.7 g.) and a solution (13 ml.) of N-trimethylsilylacetamide in methylene chloride (1 mole/372 ml.), and then the mixture was stirred. To the solution was added the solution obtained above all at once under cooling, and the reaction mixture was stirred for 2.75 hours at the same temperature. The reaction mixture was concentrated, and to the residue was added water. The powder precipitiated by scrubbing the wall of a vessel was collected by filtraion and washed with water to give 7-{DL-2-(2-thienyl)-2-nicotinoyloxyacetamido}-3-methyl-3-cephem-4-carboxylic acid (2.8 g.). This material was dissolved in an aqueous solution of sodium bicarbonate (pH 7.), and an insoluble material was filtered off. The filtrate was adjusted to pH 3 with 1N-hydrochloric acid, and the precipitate was collected by filtration. The precipitate was dissolved in a mixture of water (40 ml.) and acetone (50 ml.) under heating. The solution was treated with charcoal powder, and to the solution was added water (20 ml.). The mixture was allowed to stand in a freezer. The precipitated crystals were collected by filtration to give purified object compound, m.p. 155° to 163° C (dec.).

EXAMPLE 6

To a solution of 7-(D-2-phenyl-2-nicotinoyloxyacetamido)cephalosporanic acid (3.1 g.) and sodium bicarbonate (0.51 g.) in a mixture of acetone (9 ml.) and water (60 ml.) was introduced methanethiol gas under ice-cooling which was generated by adding 10% sulfuric acid to a sodium methanethiolate aqueous solution (including 20% methanethiol). The solution placed in a sealed tube was heated for 2 hours in an oil bath of 80° ~ 83° C and was allowed to stand for overnight at room temperature. The precipitated crystals were collected by filtration and washed with water and acetone in turn to give 7-(D-2-phenyl-2-nicotinoyloxyacetamido)-3-methylthiomethyl-3-cephem-4-carboxylic acid (0.9 g.). The crystals were dissolved in a sodium bicarbonate aqueous solution, and then insoluble materials were removed off. To the solution was added 10% hydrochloric acid and precipitated substance was collected by filtration to give the purified object compound, m.p. 223° to 224° C (dec.).

EXAMPLE 7

A solution of DL-2-(2-thienyl)-2-cinnamoyloxyacetic acid (2.8 g.), N,N-dimethylformamide (0.8 g.) and thionyl chloride (2.4 g.) in methylene chloride (40 ml.) was cooled at −50° C. To the solution was added dried triethylamine (16 ml.) under stirring and then the mixture was stirred for 30 minutes at the same temperature. To the mixture was added all at once a solution of 7-amino-3-(1-methyl-1H-tetrazol-5-yl)thiomethyl-3-cephem-4-carboxylic acid (3.26 g.) and a solution (9.2 ml.) of N-trimethylsilylacetamide in methylene chloride (containing $4.0 \times 10^{-2}$ mole) in methylene chloride (30 ml.). The reaction mixture was stirred for 30 minutes at −40° ~ −50° C, and for 2 hours at −10° ~ −20° C, and then the reaction temperature was elevated at room temperature. The solvent was distilled off from the reaction mixture under reduced pressure. To the residue was added water (30 ml.), and extracted with ethyl acetate (100 ml. × 2). The extract was washed with water and dried, and then the solvent was distilled off under reduced pressure to give oily substance. To the substance was added ether (100 ml.) and allowed to stand for overnight to give 7-[DL-2-(2-thienyl)-2-cinnamoyloxyacetamido]-3-(1-methyl-1H-tetrazol-5-yl)thiomethyl-3-cephem-4-carboxylic acid (3.0 g.).

U.V.: $\lambda_{max}$ phosphate buffer (pH 6.4) 280 mµ E=460

N.M.R.: $\delta_{ppm}$ (CD3) CO2: 4.0 (3H,S), 3.65, 3.85(2H, AB.q) 4.4 (2H,S), 6.5(1H,S) 7.3 to 7.8 (8H)

EXAMPLE 8

A solution of DL-2-(2-thienyl)-2-cinnamoyloxyacetic acid (1.4 g.), N,N-dimethylformamdie (0.4 g.) and thionyl chloride (1.18 g.) in methylene chloride (20 ml.) was cooled at −60° C. To the solution was added dried triethylamine (0.79 ml.) under stirring and then the mixture was stirred for 30 minutes. To the mixture was added all at once a solution of 7-amino-3-(5-methyl-1,3,4-thiadiazol-2-yl)thiomethyl-3-cephem-4-carboxylic acid (1.7 g.) and a solution (2.28 ml.) of N-trimethylsilylacetamide in methylene chloride (containing $2.0 \times 10^{-2}$ mole) in methylene chloride (15 ml.). The reaction mixture was stirred for 30 minutes at −40° ~ −50° C, and for 3 hours at −10° ~ −20° C, and then the reaction temperature was elevated at room temperature. The reaction solvent was distilled off from the reaction mixture under reduced pressure. To the residue was added water (50 ml.), and extracted three times with ethyl acetate (100 ml. + 50 ml. + 50 ml.). The extract was washed with water and dried, and then the solvent was distilled off under reduced pressure to give oily substance. The substance was crystalized with ether (180 ml.) to give 7-[DL-2-(2-thienyl)-2-cinnamoyloxyacetamido]-3-(5-methyl-1,3,4-thiadiazol-2-yl)thiomethyl-3-cephem-4-carboxylic acid (0.9 g.), m.p. 115° to 120° C (dec.).

U.V.: $\lambda_{max}$ phosphate buffer (pH 6.4) 280mµ, E = 510E − 9

N.M.R.: $\delta_{ppm}$ (CD3) CO2: 2.65 (3H,S), 2.5 to 2.8 (2H, m) 4.25, 4.55(2H, AB.q) 5.05 to 5.20 (1H, m) 6.48, 6.52 (1H, each S) 7.2 to 8.0 (10H, m)

EXAMPLE 9

A solution of DL-2-(2-thienyl)-2-cinnamoyloxyacetamide (2.1 g.), N,N-dimethylformamide (0.6 g.) and thionyl chloride (1.1 ml.) in methylene chloride (45 ml.) was cooled at −60° C. To the solution was added dried triethylamine (1.2 ml.) under stirring, and then the mixture was stirred for 30 minutes at the same temperature. To the mixture was added all at once a solution of 7-amino-3-(1,3,4-thiadiazol-2-yl)thiomethyl-3-cephem-4-carboxylic acid (2.6 g.) and a solution (5.1 ml.) of N-trimethylsilylacetamide in methylene chloride (containing $2.25 \times 10^{-2}$ mole) in methylene chloride (15 ml.). The reaction mixture was stirred for 30 minutes at −40° ~ −50° C, and for 3 hours at −10° ~ −20° C, and then the reaction temperature was elevated at room temperature. The reaction solvent was distilled off from the reaction mixture under reduced pressure. To the residue was added water 850 ml.) and extracted twice with ethyl acetate (120 ml. + 60 ml.). The extract was washed with water and dried over magnesium sulfate, and then the solvent was distilled off under reduced pressure to give oily substance. The substance was crystalized with ether (270 ml.) to give pale yellow powder of 7-DL-[2-(2-thienyl)-2-cinnamoyloxyacetamido]-3-(1,3,4-thiadiazol-2-yl)thiomethyl-3-cephem-4-carboxylic acid (1.7 g.).

U.V.: $\lambda_{max}$ phosphate buffer (pH 6.4) 280 mµ, E = 505

EXAMPLE 10

A mixture of D-2-phenyl-2-cinnamoyloxyacetic acid (37 g.) and thionyl chloride (100 ml.) was refluxed for an hour, and then the reaction mixture was concentrated under reduced pressure. To one-third volume of the residue was added dried acetone (100 ml.). To the mixture was dropwise added a solution of 7-amino-3-methyl-3-cephem-4-carboxylic acid (8.6 g.), sodium bicarbonate (1.3 g.), water 8200 ml.) and acetone 8120 ml.) under stirring and ice-cooling over 30 minutes. The reaction mixture was stirred for 1.5 hours at the same temperature and 2 hours at room temperature, and then concentrated. To the residue was added 10% hydrochloric acid to acidify, and then the mixture was extracted with ethyl acetate (1l.). The extract was washed with water and a saturated aqueous solution of sodium chloride and dried over magnesium sulfate, and then treated with activated charcoal. The solvent was distilled off from the solution under reduced pressure. To the oily residue was added ether (300 ml.), and the mixture was stirred for overnight at room temperature. The mixture was decanted and to the residue was added a solution of sodium 2-ethylhexanoate in acetone to give amorphous pale yellow sodium 7-(D-2-phenyl-2-cinnamoyloxyacetamido)-3-methyl-3-cephem-4-carboxylate (1.6 g.), m.p. 176° – 190° C(dec.). On the other hand, the mother liquid obtained by decantation was concentrated under reduced pressure, and to the residue was added a solution of sodium 2-ethylhexanoate in acetone. The precipitate was collected by filtration and washed with ether to give the same object compound (7.9 g.).

U.V.:

$\lambda_{max}^{phosphate\ buffer\ (pH\ 6.4)}$ 276m$\mu$, E = 485

$\lambda_{inf}^{phosphate\ buffer\ (pH\ 6.4)}$ 223m$\mu$, 217 m$\mu$

EXAMPLE 11

To thionyl chloride (100 ml.) was added D-2-phenyl-2-cinnamoyloxyacetic acid (37 g.), and the mixture was refluxed for an hour, and then concentrated under reduced pressure. Dried acetone (100 ml.) was added to one-third volume of the residue. The above-obtained mixture was dropwise added to a solution of 7-amino-3-(1-methyl-1H-tetrazol-5-yl) thiomethyl-3-cephem-4-carboxylic acid (13 g.), sodium bicarbonate (13 g.), water (200 ml.) and acetone (120 ml.), under stirring and ice-cooling over 20 minutes. The mixture was stirred for 1.5 hours under ice-cooling and additionally for 2.5 hours at room temperature. The resultant mixture was concentrated under reduced pressure, and the residue was adjusted to pH 1 with 10% hydrochloric acid and then extracted with ethyl acetate (1 l.). The extract was washed with water and an aqueous saturated solution of sodium bicarbonate, dried over magnesium sulfate, and then treated with activated charcoal. The solvent was distilled off from the solution under reduced pressure. To the gummy residue was added ether (500 ml.) and the mixture was stirred for overnight at room temperature. The precipitate was filtered to give pale yellow powder (5.0 g.) of 7-(d-2-phenyl-2-cinnamoyloxyacetamido)-3-(1-methyl-1H-tetrazol-5-yl)thiomethyl-3-cephem-4-carboxylic acid, mp 145° C (dec.). The product was changed to its sodium salt, mp 181° to 183° C (dec.) by conventional method.

U.V.:

$\lambda_{max}^{phosphate\ buffer\ (pH\ 6.4)}$ 280m$\mu$, E = 473

$\lambda_{max}^{phosphate\ buffer\ (pH\ 6.4)}$ 216m$\mu$, 222m$\mu$

EXAMPLE 12

To a mixture of benzene (50 ml.) and thionyl chloride (15 ml.) was added D-2-phenyl-2-cinnamoyloxyacetic acid (7 g.), and the mixture was heated for 3.5 hours at 70° C, and then the excess of thionyl chloride under reduced pressure. A small amount of benzene was added to the residue, and then the solvent was distilled off from the solution. The residue was dissolved in acetone (40 ml.). The acetone solution was dropwise added to a solution of 7-amino-3-(5-methyl-1,3,4-thiadiazol-2-yl)thiomethyl-3-cephem-4-carboxylic acid (10 g.), sodium bicarbonate (10 g.), water (150 ml.) and acetone (100 ml.) under stirring and ice-cooling. The mixture was stirred for 1.5 hours under ice-cooling and additionally for overnight at room temperature. The insoluble substance in the reaction mixture was removed by filtration, and then acetone was removed from the filtrate under reduced pressure. The residue was washed with ethyl acetate (200 ml.), adjusted to pH 1.0 with concentrated hydrochloric acid, and then extracted with ethyl acetate (800 ml.) containing a little amount of acetone. The extract was washed with an aqueous saturated solution of sodium chloride, dried, and then the solvent was distilled off under reduced pressure. The residue was crystallized by adding ether to give powder (3 g.) of 7-D-2-phenyl-2-cinnamoyloxyacetamido)-3-(5-methyl-1,3,4-thiadiazol-2-yl)thiomethyl-3-cephem-4-carboxylic acid. The product was dissolved in acetone, and to the solution was added equimolar of sodium 2-ethylhexanoate give sodium salt of the object compound.

U.V.: $\lambda_{max}^{phosphate\ buffer\ (pH\ 6.4)}$ 275 m$\mu$, E = 307

EXAMPLE 13

A mixture of D-2-phenyl-2-cinnamoyloxyacetic acid (6 g.), benzene (50 ml.) and thionyl chloride (20 ml.) was stirred for 3 hours at 65° C, and the excess of thionyl chloride was distilled off under reduced pressure. To the residue was added benzene, and benzene was distilled off under reduced pressure, and then the residue was dissolved in acetone (40 ml.). The acetone solution was dropwise added to a mixture of 7-amino-3-(1,3,4-thiadiazol-2-yl)thiomethyl-3-cephem-4-carboxylic acid (10 g.) sodium bicarbonate (10 g.), water (120 ml.) and acetone (80 ml.) under stirring and ice-cooling. The mixture was stirred for 1.5 hours at the same temperature, and then for 2 hours at room temperature. The reaction mixture was filtered, and the filtrate was distilled off under reduced pressure. The residue was washed with ethyl acetate (200 ml.). The aqueous layer was separated out and adjusted to pH 1.0 with 10% hydrochloric acid, and then extracted with ethyl acetate (800 ml.). The extract was washed with saturated sodium chloride aqueous solution and dried, and then ethyl acetate was distilled off. The residue was crystalized with ether to give powder of 7-(D-2-phenyl-2-cinnamoyloxyacetamido)-3-(1,3,4-thiadiazol-2-yl)thiomethyl-3-cephem-4-carboxylic acid (2.1 g.). This substance was dissolved in acetone, and to the solution was added an equimolar of sodium 2-ethylhexanoate to give sodium salt of the substance.

U.V.: $\lambda_{max}^{phosphate\ buffer\ (pH\ 6.4)}$ 278 m$\mu$, E = 364

EXAMPLE 14

A mixture of 2-cinnamoyloxyacetic acid (10.4 g.) and thionyl chloride (50 ml.) was refluxed for 2 hours, and the excess of thionyl chloride was distilled off.

One-half Volume of the residue was dissolved in acetone (30 ml.), and the solution was dropwise added to a mixture of 7-amino-3-methyl-3-cephem-4-carboxylic acid (4.3 g.), sodium bicarbonate (6.5 g.), water (100 ml.) and acetone (60 ml.) under stirring and ice-cooling over 10 minutes. The reaction mixture was stirred for 1.5 hours under ice-cooling and for 2 hours at room temperature. The reaction mixture was filtered, and the filtrate was concentrated under reduced pressure. The residue was washed with ethyl acetate. An aqueous layer was separated out and adjusted to pH 2 with 10% hydrochloric acid, and then extracted with ethy acetate (500 ml.). The extract was washed with water and a saturated sodium chloride aqueous solution, dried over magnesium sulfate. The solution was treated with activated charcoal, and then the solvent was distilled off under reduced pressure. The oily pale yellow residue was crystalized with ether (300 ml.) to give white crystals of 7-(2-cinnamoyloxyacetamido)-3-methyl-3-cephem-4-carboxylic acid (1.2 g.).

U.V.:

$\lambda_{max}^{phosphate\ buffer\ (ph(6\cdot 4)}$ 276m$\mu$, E = 606

$\lambda_{inf}^{phosphate\ buffer\ (ph(6\cdot 4)}$ 217m$\mu$, 222 m$\mu$

EXAMPLE 15

A acetone solution (40 ml.) of 2-cinnamoyloxyacetyl chloride was prepared by using the similar precedure of example 8. The solution was dropwise added to a mixture of 7-amino-3-(1,3,4-thiadiazol-2-yl)thiomethyl-3-cephem-4-carboxylic acid (6.6 g.), sodium bicarbonate (6.5 g.), water (150 ml.) and acetone (60 ml.) under stirring and ice-cooling over 10 minutes. The reaction mixture was stirred for 1.5 hours under ice-cooling and then for 2.5 hours at room temperature. The reaction mixture was concentrated and the residue was washed with ethyl acetate. The aqueous layer was separated out and adjusted to pH 1 with 10% hydrochloric acid and extracted with ethyl acetate (700 ml.). The extract was washed with water and a saturated sodium chloride aqueous solution, and then dried over magnesium sulfate. The solution was treated with activated charcoal, and the solvent was distilled off. The oily pale yellow residue was crystalized with ether (300 ml.) to give pale yellow powder of 7-(2-cinnamoyloxyacetamido)-3-(1,3,4-thiadiazol-2-yl)thiomethyl-3-cephem-4-carboxylic acid (4.5 g.). This substance was recrytalized from acetone to give purified white crystals, m.p. 165° – 168° C (dec.).

U.V.:

$\lambda_{max}^{phosphate\ buffer\ (ph(6\cdot 4)}$ 279m$\mu$, E=639

$\lambda_{inf}^{phosphate\ buffer\ (ph(6\cdot 4)}$ 217m$\mu$, 222 m$\mu$

EXAMPLE 16

D,L-2-(2-Thienyl)-2-nicotinoyloxyacetic acid (1 g.) was reacted with 7-amino-3-(5-methyl-1,3,4-thiadiazol-2-yl)thiomethyl-3-cephem-4-carboxylic acid (1.2 g.), in a similar manner to that of Example 5, to give 7-[D,L-2-(2-thienyl)-2-nicotinoyloxyacetamido]-3-(5-methyl-1,3,4-thiadiazol-2-yl)-thiomethyl-3-cephem-4-carboxylic acid (1.27 g.), m.p. 149° to 151° C (dec.).

EXAMPLE 17

(Chloromethylene)dimethylammonium chloride was prepared from dimethylformamide (0.88 g.) and thionyl chloride (1.31 g.) according to a conventional method, was suspended in methylene chloride (30 ml.). To this suspension, was added hydrochloric acid salt (2.93 g.) of DL-2-phenyl-2-picolinoyloxy-acetic acid (2.93 g.) under ice-cooling and the mixture was stirred for 2.5 hours at room temperature. To this mixture was added all at once a mixture of 7-amino-3-(1-methyl-1H-tetrazol-5-yl)thiomethyl-3-cephem-4-carboxylic acid (3.28 g.), a solution (13 ml.) of N-trimethylsilylacetamide in methylene chloride (1 mole/372 ml.) and methylene chloride (40 ml.) with stirring vigorously under ice-cooling. The resultant reaction mixture was further stirred under ice-cooling for 3.5 hours. The solvent was distilled off from the reaction mixture under reduced pressure and then the residue was added with ice-water (200 ml.) and exteacted with total volume 300 ml. of ethyl acetate. The ethyl acetate layer was back-extracted with a dilute sodium bicarbonate aqueous solution and then the aqueous layer was ajdusted to pH 3 with a dilute hydrochloric acid and back-extracted with ethyl acetate. The organic layer was washed with a saturated aqueous solution of sodium chloride and dried over magnesium sulfate. Pale yellow powder given by removal of the solvent was recrystallized from ethyl acetate to give 7-(DL-2-phenyl-2-picolinoyloxyacetamido)-3-(1-methyl-1H-tetrazol-5-yl)thiomethyl-3-cephem-4-carboxylic acid (1.97 g.), m.p. 140° to 142° C (dec.).

EXAMPLE 18

A mixture of dimethylformamide (0.53 g.) and thionyl chloride (3.0 ml.) was heated for 30 minutes at 50° C, and the excess of thionyl chloride was distilled off under reduced pressure. Ether was added to the residue, and the mixture was allowed to stand for a while and then the solvent was distilled off, which were repeated twice. And then the similar operations were repeated twice by using methylene chloride instead of ether. Thus obtained crystals were suspended in methylene chloride (30 ml.), and to the suspension was added hydrochloric acid salt (2.1 g.) of D-2-phenyl-2-nicotinoyloxyacetic acid under ice-cooling, and then the mixture was stirred for 2.5 hours at room temperature.

On the other hand, to methylene chloride (36 ml.) was added a mixture of 7-amino-3-(1-methyl-1H-tetrazol-5-yl)-methylthio-3-cephem-4-carboxylic acid (2.0 g.) and a solution (7.7 ml.) of N-trimethylsilylacetamide in methylene chloride (1 mole/372 ml.), and the resultant mixture was stirred for 3 hours at room temperature.

To the solution was added the solution obtained above all at once under ice-cooling, and then the mixture was stirred for 2 hours at the same temperature. The reaction mixture was concentrated at a low temperature. To the residue was added ice-water followed by operations of scrubbing the wall of a vessel and decantation which were repeated several times. Thus obtained powder was collected by filtration, washed with water and dried to give 7-(D-2-phenyl-2-nicotinoyloxyacetamido)-3-(1-methyl-1H-tetrazol-5-yl)thiomethyl-3-cephem-4-carboxylic acid (3.25 g.). This substance was suspended in water, dissolved therein by being adjusted to pH 7.5 with a sodium bicarbonate aqueous solution. The resultant solution was treated with activated carbon and adjusted to pH 2 with 1N hydrochloric acid. The precipitate was collected by filtration, washed with water and dried to give the pure product, m.p. 145° to 150° C (dec.).

EXAMPLE 19

A mixture of dimethylformamide (0.44 g.) and thionyl chloride (2.5 ml.) was stirred for 30 minutes at 50°

C, and then the excess of thionyl chloride was distilled off under reduced pressure. Ether was added to the residue, and the mixture was allowed to stand for a while and then the solvent was distille off, which were repeated twice. And then the similar operations were repeated twice by using methylene chloride instead of ether. Thus obtained white substance was suspended in methylene chloride (25 ml.), and to the suspension was added hydrochloric acid salt (1.47 g.) of DL-2-phenyl-2-isonicotinoyloxyacetic acid under ice-cooling, and then the mixture was stirred for 2.5 hours at room temperature.

On the other hand, to methylene chloride (30 ml.) were added 7-amino-3-(1-methyl-1H-tetrazol-5-yl)thiomethyl-3-cephem-4-carboxylic acid (1.65 g.) and a solution (6.4 ml.) of N-trimethylsilylacetamide in methylene chloride (1 mole/ 372 ml.), and then the mixture was stirred for 3 hours at room temperature. To the solution was added the solution obtained above all at once under cooling, and the reaction mixture was stirred for 1.5 hours at the same temperature. The reaction mixture was concentrated, ice-water was added to the residue, the wall of vessel was scrubbed and the mixture was decanted. This operation was repeated several times, and thus obtained powder was collected by filtration, washed with water and dried to give 7-(D-2-phenyl-2-isonicotinoyloxyacetamido)-3-(1-methyl-1H-tetrazol-5-yl)thiomethyl-3-cephem-4-carboxylic acid (2.1 g.), m.p. 145° to 150° C (dec.).

EXAMPLE 20

A mixture of dimethylformamide (0.88 g.) and thionyl chloride (20 ml.) was heated at 50° C on an oil bath for an hour, and then the excess of thionyl chloride was distilled off under reduced pressure. Ether was added to the residue and the mixture was allowed to stand for a while and then the solvent was distilled off, which were repeated twice. And then the similar operations were repeated twice by using methylene chloride instead of ether. The residue was suspended in methylene chloride (30 ml.), and to the suspension was added hydrochloric acid salt (2.93 g.) of DL-2-phenyl-2-picolinoyloxyacetic acid under ice-cooling, and then the mixture was stirred for 2 hours at room temperature.

On the other hand, to methylene chloride (30 ml.) were added 7-amino-3-(5-methyl-1,3,4-thiadiazol-2-yl)thiomethyl-3-cephem-4-carboxylic acid (3.38 g.) and a solution (13 ml.) of N-trimethylsilylacetamide in methylene chloride (1 mole/372 ml.), and the mixtures was stirred for 4 hours at room temperature. To the solution was added the solution obtained above all at once under cooling with dry ice and acetone, and the reaction mixture was stirred for 3.25 hours. The reacting mixture was concentrated and to the residue was added ice-water. The powder preciptitated by scrubbing the wall of a vessel was collected by filtration, washed with water and suspended in water. The suspension was adjusted to pH 6 with a dilute sodium bicarbonate aqueous solution and dissolved into the solution. After removal of an insoluble substance by filtration, the filtrate was adjusted to ph 3.5 with 1N-hydrochloric acid. The appearing precipitate was collected by filtration and washed with water to give 7-(DL-2-phenyl-2-picolinoyloxyacetamido)-3-(5-methyl-1,3,4-thiadiazol-2-yl)thiomethyl-3-cephem-4-carboxylic acid (4.7 g.). This substance was suspended in water and dissolved into the solution by addition of a sodium bicarbonate aqueous solution, and an insoluble material was filtered off. The filtrate was adjusted to pH 3.5 with 1N-hydrochloric acid, and the precipitate was collected by filtration and washed to give the pure product, m.p. 125° to 135° C (dec.).

EXAMPLE 21

A mixture of dimethylformamide (0.77 g.) and thionyl chloride (1.5 ml.) was heated for 10 minutes at room temperature, and then the excess of thionyl chloride was distilled off under reduced pressure. Methylene chloride was added to the residue and the mixture was allowed to stand for a while and then the solvent was distilled off to give crystals. Thus obtained crystals were suspended in methylene chloride (20 ml.), and to the suspension was added with stirring hydrochloric acid salt (2.82 g.) of D-2-phenyl-2-nicotinoyloxyacetic acid under ice-cooling, and then the mixture was stirred for 2.5 hours at room temperature.

On the other hand, to methylene chloride (30 ml.) were added 7-amino-3-(3-methyl-1,2,4-thiaziazol-5-yl)thiomethyl-3-cephem-4-carboxylic acid (3.0 g.) and a solution (13 ml.) of N-trimethylsilylacetamide in methylene chloride (1 mole/372 ml.), and then the mixture was stirred for 2 hours at room temperature. To the solution was added the solution obtained above all at once at −10° C under stirring, and then the mixture was stirred for 2.5 hours at 0° to 5° C and concentrated. To the residue were added ice-water and ethyl acetate, and an insoluble material was filtered off. The ethyl acetate layer was separated out and extracted with the saturated aqueous solution of sodium bicarbonate. The alkaline layer was adjusted to pH 2 to 3 with 10% hydrochloric acid, and the precipitate was collected by filtration, washed with water and dried to give 7-(DL-2-phenyl-2-picolinoyloxyacetamido)-3-(3-methyl-1,2,4-thiadiazol-5-yl)thiomethyl-3-cephem-4-carboxylic acid (4.3 g.), m.p. 150° to 160° C (dec.).

EXAMPLE 22

In a similar manner to that of Example 6, the following compounds were obtained:
1. 7-(Dl-2-Phenyl-2-picolinoyloxyacetamido)-3-(1-methyl-1H-tetrazol-5-yl)thiomethyl-3-cephem-4-carboxylic acid, m.p. 140° to 142° C (dec.).
2. 7-(DL-2-Phenyl-2-picolinoyloxyacetamido)-3-(5-methyl-1,3,4-thiadiazol-2-yl)thiomethyl-3-cephem-4-carboxylic acid, m.p. 125° to 135° C (dec.).
3. 7-(DL-2-Phenyl-2picolinoyloxyacetamido-3-(3-methyl-1,2,4-thiadiazol-5-yl)thiomethyl-3-cephem-4-carboxylic acid, m.p. 150° to 160° C (dec.).
4. 7-(D-2-Phenyl-2-nicotinoyloxyacetamido)-3-(1-methyl-1H-tetrazol-5-yl)thiomethyl-3-cephem-4-carboxylic acid, m.p. 145° to 150° C. (dec.).
5. 7-(D-2-Phenyl-2-isonicotinoyloxyacetamido)-3-(1-methyl-1H-tetrazol-5-yl)thiomethyl-3-cephem-4-carboxylic acid, m.p. 145° to 150° C (dec.).

I claim:
1. A compound of the formula:

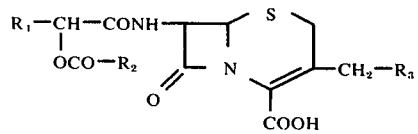

wherein
R₁ is phenyl or thienyl,
R₂ is pyridyl, and
R₃ is thiadiazolylthio or tetrazolylthio, either of which may be substituted with methyl,
and pharmaceutically acceptable salts thereof.

2. A compound according to claim 1, wherein R₁ is phenyl.

3. A compound according to claim 2, wherein R₃ is methyl-substituted.

4. A compound according to claim 3, wherein
R₂ is 2-pyridyl, and
R₃ is 5-methyl-1,3,4-thiadiazol-2-ylthio or 3-methyl-1,2,4-thiadiazol-5-ylthio.

5. A compound according to claim 3, wherein R₃ is 1-methyl-1H-tetrazol-5-ylthio.

6. A compound according to claim 1, wherein
R₁ is thienyl, and
R₃ is thiadiazolylthio which may be substituted with methyl.

7. A compound according to claim 6, wherein R₃ is methyl-susbstituted.

8. A compound according to claim 7, wherein
R₂ is 3-pyridyl, and
R₃ is 5-methyl-1,3,4-thiadiazol-2-ylthio.

* * * * *

UNITED STATES PATENT AND TRADEMARK OFFICE
CERTIFICATE OF CORRECTION

PATENT NO. : 4,001,225
DATED : January 4, 1977
INVENTOR(S) : Hirokichi Harada

It is certified that error appears in the above-identified patent and that said Letters Patent are hereby corrected as shown below:

```
Column 1, line 30, before "pyridine" insert --tetrazole,--;
Column 3, line 67, after "its" delete "their";
Column 4, line 41, "trialkylaine" should read --trialkylamine--;
Column 5, line 62, after "treated" delete "with" and
          insert --in--;
Column 10, line 6, "(CD3) CO2" should read --(CD3)2 CO--;
           line 36, "E=510E-9" should read --E=510--;
           line 37, "(CD3) CO2" should read --(CD3)2 CO--;
           line 59, "850 ml.)" should read --(50 ml.)--;
Column 11, line 10, "8200 ml.)" should read --(200 ml.)--;
           line 11, "8120 ml.)" should read --(120 ml.)--;
           lines 57-58, "charchoal" should read --charcoal--;
           line 62, "7-(d-2-" should read -- 7-(D-2- --;
Column 16, line 50, "2picolinoyloxyacetamido" should read
           --2-picolinoyloxyacetamido--.
```

Signed and Sealed this

Ninth Day of May 1978

[SEAL]

Attest:

RUTH C. MASON
Attesting Officer

LUTRELLE F. PARKER
Acting Commissioner of Patents and Trademarks